United States Patent [19]
McSpadden

[11] Patent Number: 5,275,562
[45] Date of Patent: Jan. 4, 1994

[54] METHOD AND MATERIAL FOR OBTURATING AN EXTIRPATED ROOT CANAL

[76] Inventor: John T. McSpadden, 6918 Shallowford Rd., Chattanooga, Tenn. 37421

[21] Appl. No.: 825,955

[22] Filed: Jan. 27, 1992

Related U.S. Application Data

[63] Continuation-in-part of Ser. No. 532,588, Jun. 4, 1990, Pat. No. 5,083,923.

[51] Int. Cl.$^5$ .................. A61C 5/02; A61G 5/02
[52] U.S. Cl. ........................................ 433/224
[58] Field of Search .................... 433/81, 83, 224

[56] References Cited

U.S. PATENT DOCUMENTS

| | | | |
|---|---|---|---|
| 4,353,698 | 10/1982 | McSpadden | 433/164 |
| 4,457,710 | 7/1984 | McSpadden | 433/81 |
| 4,681,545 | 7/1987 | Lapcevic | 433/224 |
| 4,894,011 | 1/1990 | Johnson | 433/81 |
| 4,931,096 | 6/1990 | Fujisawa et al. | 433/224 |
| 5,051,093 | 9/1991 | Fitzmorris | 433/224 |
| 5,067,900 | 11/1991 | McSpadden | 433/81 |
| 5,083,923 | 1/1992 | McSpadden | 433/81 X |
| 5,088,927 | 2/1992 | Lee | 433/224 |

OTHER PUBLICATIONS

Grassi, Michael D., et al; Changes in the Physical Properties of the Ultrafil Low-Temperature (70°) Thermoplasticized Gutta-Percha System; *Journal of Endodontics;* vol. 15, No. 11, Nov. 1989; pp. 517-521.

*Primary Examiner*—Gene Mancene
*Assistant Examiner*—Nicholas D. Lucchesi
*Attorney, Agent, or Firm*—Luedeka, Hodges, Neely & Graham

[57] ABSTRACT

A method of obturating an extirpated root canal and an associated filler material utilizes two classes of gutta-percha, one class of which becomes plasticized at a predetermined temperature and the other class of which becomes plasticized at a temperature which is less than the predetermined temperature. In one embodiment of the method, the second class of gutta-percha is coated about the first class when in a plasticized condition, and in another embodiment of the method, the second class is pre-coated about the first class and the second class is heated to plasticized condition without plasticizing the first class. In either case, the first class of gutta-percha supports the plasticized second class when subsequently introduced into a root canal for filling the canal. To increase the rigidity of the first class of gutta-percha, the first class may be coated with a cured layer of methyl methacrylate before the second class of gutta-percha is coated about the first class. Following introduction of the two classes of gutta-percha into the canal, the classes may be condensed within the root canal system.

26 Claims, 3 Drawing Sheets

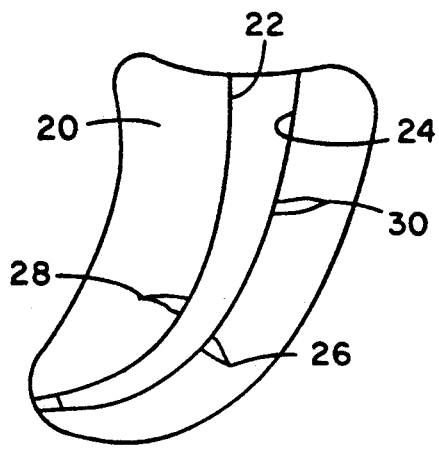
Fig. 1
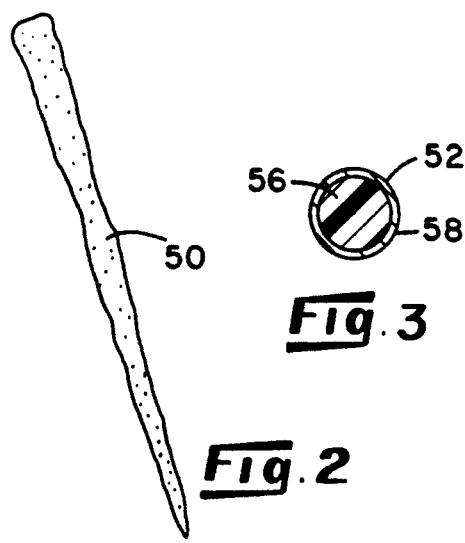
Fig. 2
Fig. 3
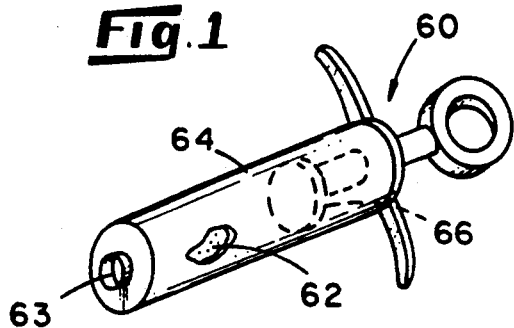
Fig. 4
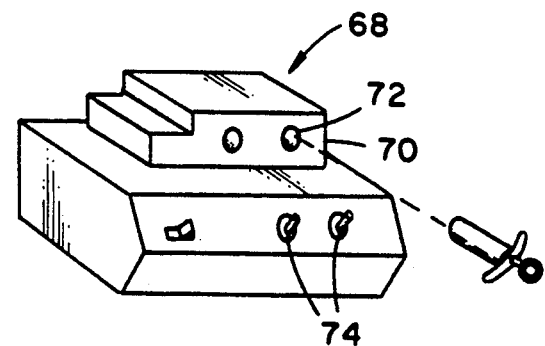
Fig. 5
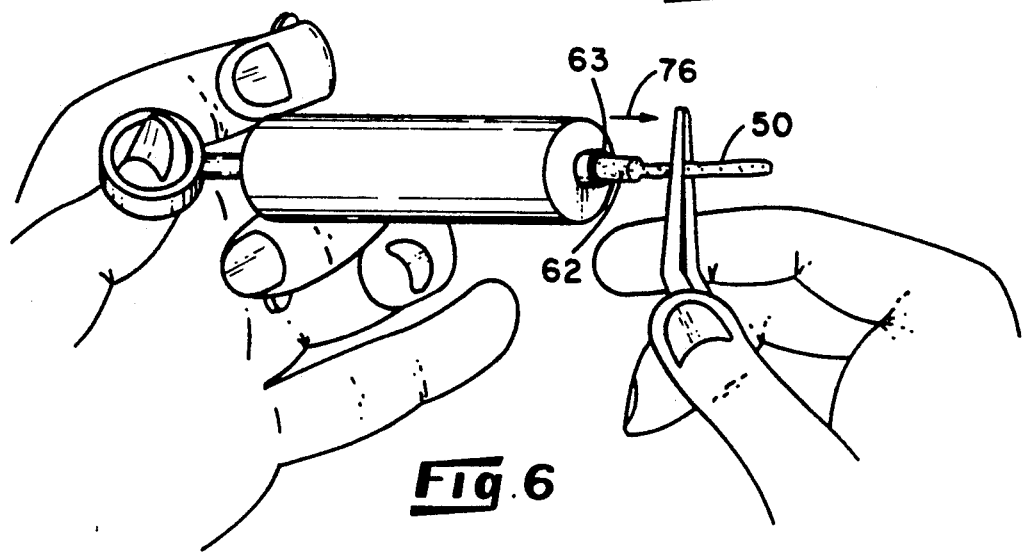
Fig. 6

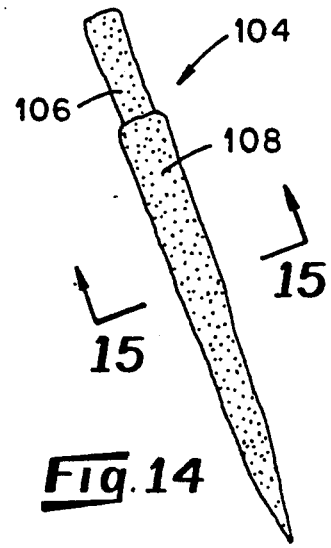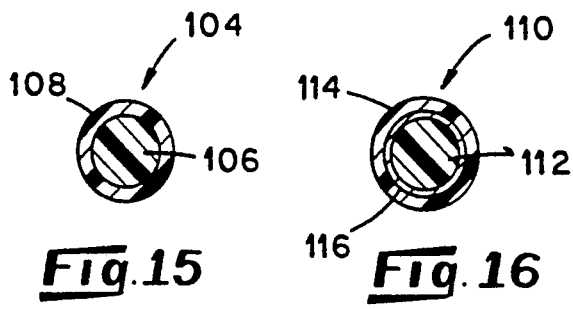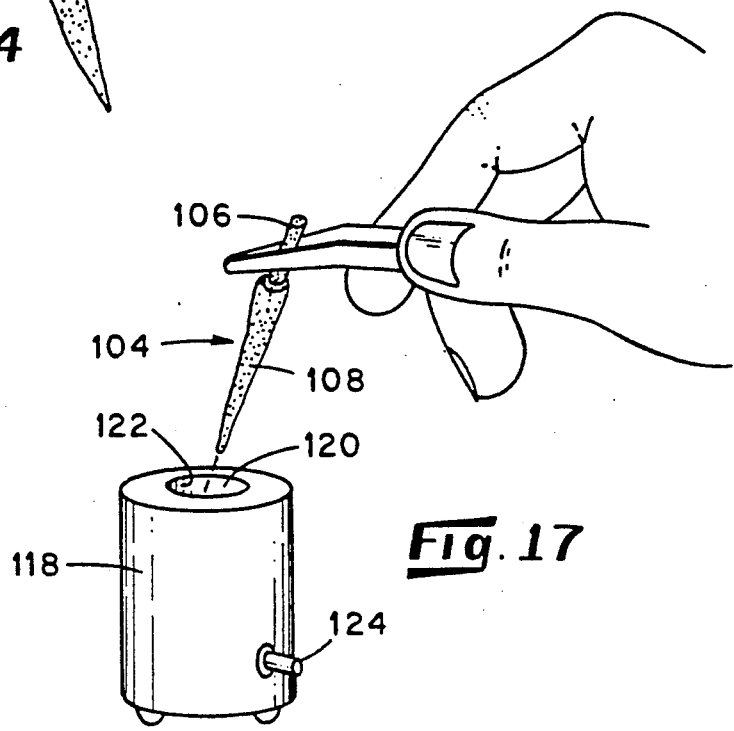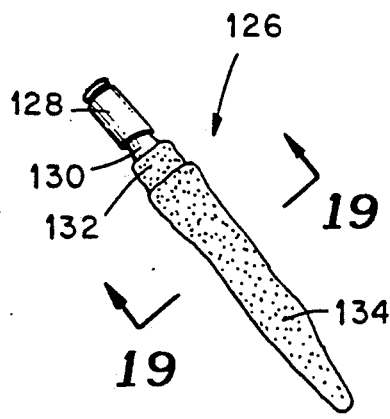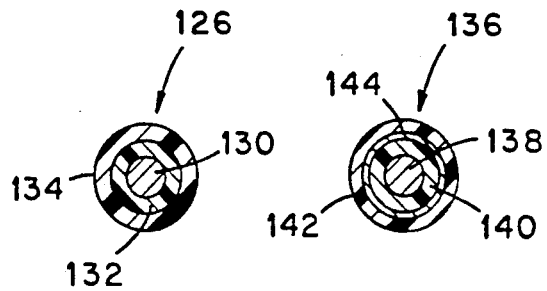

METHOD AND MATERIAL FOR OBTURATING AN EXTIRPATED ROOT CANAL

This application is a continuation-in-part application of application Ser. No. 07/532,588 filed Jun. 4, 1990 and entitled METHOD OF OBTURATING AN EXTIRPATED ROOT CANAL now U.S. Pat. No. 5,083,923, the disclosure of which is incorporated herein by reference.

BACKGROUND AND SUMMARY OF THE INVENTION

The present invention relates generally to the field of endodontics and relates more particularly to processes for filling stripped root canals and materials with which stripped root canals are filled.

In co-pending application serial number 07/532,588, identifying the same inventor as the instant application, there is described a method for obturating an extirpated root canal utilizing two types of filler materials wherein one type of filler material is provided in the form of a gutta-percha point having a predetermined melting temperature and wherein the other type of filler material is provided in the form of a thermo-plasticized gutta-percha having a melting temperature which is several degrees less than that of the melting temperature of the gutta-percha point. Steps involved in the method of the referenced application include the positioning of a portion of a gutta-percha point within a root canal and then introducing an amount of the gutta-percha possessing the lower melting temperature in a heated, softened condition into the root canal. The thermoplasticized gutta-percha is then manipulated into contact with the portion of the gutta-percha point positioned within the root canal so that the gutta-percha point is fed into and compacted within the root canal with the amount of the other gutta-percha.

Because the gutta-percha possessing the lower melting temperature is a fluid when introduced into the root canal, the apical foramen and any fissures or voids associated with the canal wall are suitably coated and/or filled by this gutta-percha with no need that filler material be forcibly urged, such as by reciprocating motions of a compacting instrument, into the canal. Thus, the endodontist performing the aforedescribed method need not possess as high a degree of skill as in prior methods in order to satisfactorily fill the root canal, and the possibility that the apical foramen will be extruded by filler material is reduced by the aforedescribed method. In addition, the heat necessary for softening and rendering workable the gutta-percha point material is absorbed by the point material from the heat of the softened gutta-percha material in contact therewith, and any need for the manipulation of a high-speed rotating instrument within the canal for the purpose of generating frictional heat is obviated.

It is an object of the present invention to provide a new and improved method for obturating an extirpated root canal which provides the advantages obtained with the use of gutta-percha materials possessing different melting temperatures and which facilitates the introduction of the gutta-percha having the lower melting temperature into a root canal when in a heated and softened condition.

Another object of the present invention is to provide a new and improved filler material for use with the method of the invention.

More particularly, the present invention is directed to a method of obturating an extirpated root canal with a first amount of gutta-percha which becomes plasticized at a predetermined temperature and a second amount of gutta-percha which becomes plasticized at a temperature which is less than the predetermined temperature, and a filler material utilizing the first and second amounts.

In one embodiment of the method, the first amount of gutta-percha is provided and then coated with the second amount of gutta-percha in a plasticized condition and at a preselected temperature wherein the preselected temperature is less than the temperature at which the first amount becomes plasticized so that the first amount remains in a relatively firm condition while the plasticized second amount remains coated thereabout. The first and second amounts are then introduced together into a root canal where they are used to fill the canal. In this one embodiment, the first amount may be provided as a point possessing sufficient rigidity with the second amount coated thereupon so as to act as a carrier for the introduction of the second amount into the canal, or the first amount may be coated upon the shank of a shanked carrier so that the introduction of the first and second amounts into the root canal is effected as the carrier is inserted into the canal.

In another embodiment of the method, there is provided a filler material including the first amount of gutta-percha and the second amount of gutta-percha coated about the first amount wherein both the first and second amounts are in a relatively firm condition. The filler material is then heated so that the second amount becomes plasticized but the first amount remains in a relatively firm condition. The filler material is then introduced into a root canal where the first and second amounts are used to fill the canal. In this another embodiment, the filler material may be provided in the form of a point wherein its first amount possesses sufficient rigidity so as to act as a carrier for the introduction of the second amount into the canal, or the filler material, including both of its first and second amounts, may be coated upon the shank of a shanked carrier so that the introduction of the first and second amounts into the root canal is effected as the carrier is inserted into the canal.

BRIEF DESCRIPTION OF THE DRAWINGS

FIG. 1 is a cross-sectional view of a tooth having an extirpated root canal prepared for filling in accordance with the method of this invention;

FIG. 2 is a perspective view of a gutta-percha point utilized in one embodiment of the method of this invention;

FIG. 3 is a cross-sectional view of a gutta-percha point like that of FIG. 2 which has been coated with a layer of methyl methacrylate.

FIG. 4 is a perspective view of an apparatus, shown partially cut-away, containing gutta-percha possessing a lower plasticizing temperature than the gutta-percha of the FIG. 2 point.

FIG. 5 is a perspective view of a heating appliance with which the gutta-percha contained within the FIG. 4 apparatus can be heated and illustrating the FIG. 4 apparatus when removed from the heating appliance.

FIGS. 6-9 are views illustrating in sequence various steps involved in filling the root canal of FIG. 1 with the gutta-percha point of FIG. 2 and the gutta-percha contained within the apparatus of 4.

FIG. 14 is a view of a filler material including two gutta-percha materials possessing different plasticizing temperatures.

FIG. 15 is a cross-sectional view taken along line 15—15 of FIG. 14.

FIG. 16 is a cross-sectional view of a filler material like that of FIG. 14 having a layer of methyl methacrylate interposed between its gutta-percha materials.

FIG. 17 is a perspective view of a heating apparatus with which the filler material of FIG. 14 may be heated and illustrating the FIG. 14 material when removed from the apparatus.

FIG. 18 is a perspective view of a carrier upon which two classes of gutta-percha materials are coated.

FIG. 19 is a cross-sectional view taken about along line 18—18 of FIG. 17.

FIG. 20 is a cross-sectional view of a carrier, with filler material, like that of FIG. 17 having a layer of methyl methacrylate interposed between its gutta-percha materials.

DETAILED DESCRIPTION OF THE ILLUSTRATED EMBODIMENTS

Figure 7:
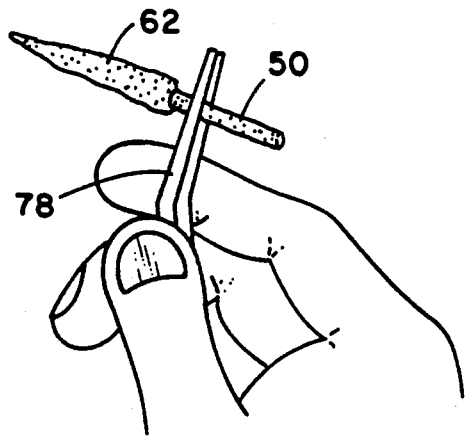

Turning now to the drawings in greater detail, there is illustrated in FIG. 1 a tooth 20 having a root canal 22 which has been extirpated (stripped) in preparation of an obturating (filling) process in accordance with an embodiment of the method of the invention. The root canal 22 has been extirpated in accordance with well-known procedures which remove dead or damaged tissue from the canal 22 in order to provide a space 24 for accepting filler material inserted and compacted therein. In the depicted tooth 20, there are illustrated fissures 26, 28, 30 defined within the wall of the root canal 22 which are ordinarily difficult to fill by conventional obturating processes. As will be apparent herein, by feeding and compacting two gutta-percha materials having different plasticizing temperatures within the root canal 22 in accordance with the steps of this invention, the entire space 24 of the root canal 22 and the fissures 26, 28, 30 defined along the root canal wall are completely filled with gutta-percha.

Both the method and the filler material of the invention utilize two classes, or amounts, gutta-percha materials having different plasticizing temperatures. As used herein, the term "plasticizing temperature" refers to the temperature at which the gutta-percha material, when exposed to a rise in temperature, melts from a solid, relatively firm condition to a softened, fluid-like condition possessing little resistance to forces which may tend to deform the material and which is capable of easily conforming in shape to the shape of a container within which the material may be held.

It follows that one class of the two classes of gutta-percha materials discussed herein possesses a plasticizing temperature which is lower than that of the other class of the two classes of gutta-percha materials, but both may originate from a similar material state. For example, gutta-percha in its material state is known to possess a plasticizing temperature of about 200° F., but may be treated in order to render a gutta-percha form having a lower plasticizing temperature. Such treatment involves the heating of the gutta-percha to an elevated temperature and subsequently cooling the gutta-percha at a controlled rate. For example, an amorphous gutta-percha composition containing primarily an "alpha" crystalline form of gutta-percha when in an untreated state may experience a change during treatment so that at the end of treatment, a gutta-percha composition contains primarily a "beta" crystalline form of gutta-percha having a lower plasticizing temperature. The process by which a composition of gutta-percha can be changed to thereby lower its plasticizing temperature is known so that more detailed description of the process is not believed to be necessary.

When filling a root canal with the two classes gutta-percha materials possessing different plasticizing temperatures in accordance with a method described herein, the two materials are manipulated together within the root canal so as to become compacted therein. The differential between the plasticizing temperatures of the two gutta-percha materials may be within a relatively broad range but is preferably large enough to provide a workable differential between the two plasticizing temperatures and preferably not so large that the quality of either of the two classes of materials is jeopardized for purposes of filling a root canal. A temperature differential between the two plasticizing temperatures believed to be best suited for purposes of the present invention will fall within the range of about 10 to 20 Centigrade degrees. Furthermore, when the class of gutta-percha possessing the lower plasticizing temperature is heated to its plasticized condition in accordance with an embodiment of the method of this invention, its temperature is low enough so that the tissue of the patient's mouth is not likely to be harmed when the plasticized gutta-percha is placed thereagainst, and this plasticized gutta-percha possesses a tackiness which is well-suited for adhering to the other class of gutta percha as will be apparent herein.

In accordance with one embodiment of the method described herein, an amount of the first gutta percha material (i.e., the material with the higher plasticizing temperature) is to be provided in the form of a strand-like piece of gutta-percha, commonly known as a point and indicated 50 in FIG. 2. The first gutta-percha material comprising the point 50 is solid in form at room temperature, e.g., about 24° C., so that heat must be applied to the material in order to render the material soft and pliable for compaction within a root canal. As will be apparent herein, an amount of the second gutta-percha is coated about the point 50 in a heated, plasticized condition so that when used to fill a root canal, the point 50 acts as a carrier for introducing both the first and second gutta-percha amounts into a root canal. Accordingly, it is desirable that the point 50 possess a sufficient degree of rigidity, when exposed to the weight and heat of the plasticized gutta-percha borne thereby, for transporting the second gutta-percha amount into the root canal without any appreciable deformation of the point 50.

It has been found that the rigidity of the first amount of gutta-percha may be enhanced by a rigidifying material, such as a cured layer of methyl methacrylate positioned, or coated, about the first amount. There is illustrated in FIG. 3 the cross section of an alternative point 52 including a core 56 comprised of the first class of gutta-percha material and an outer layer 58 comprised of methyl methacrylate. As shown in FIG. 3, the layer 58 of methyl methacrylate is relatively thin in relation to the diameter of the core 56. With the cured layer 58 positioned about the core 56, the point 52 possesses a greater degree of rigidity than would be possessed by the core 56, by itself (i.e., without the layer 58). When the point 52 is subsequently coated with a plasticized amount of the second class of gutta-percha, the layer 58 helps to maintain the rigidity of the point 52 under the heat and weight of the amount of the second class of gutta-percha to reduce the likelihood of any appreciable deformation of the point 52 before it is introduced into a canal.

Another advantage provided by the methyl methacrylate layer 58 relates to the fact that the layer 58 insulates, to a degree, the core 56 from the heat of the plasticized amount of the second class of gutta-percha coated about the point 52. It has been found that the provision of the layer 58 does not adversely effect the void-filling characteristics of the material of the core 56, and that the subsequently-applicant plasticized amount of gutta-percha is permitted to bond to the gutta-percha core 56 through the layer 58. The layer 58 may be applied to, or coated upon, the core 56 in, for example, a dipping operation while the methyl methacrylate is in an uncured condition and then permitted to harden to its cured condition about the core 56.

It will be understood that the rigidity of a point, such as the point 52 of FIG. 3, may depend largely upon the diameter of its core. Generally, the smaller the diameter of its core, the less rigidity that the core may possess. Accordingly, the thickness of the layer 58 of methyl methacrylate coated about the core 56 is greater in points having cores 56 of smaller diameter so that the point retains sufficient rigidity for suitably supporting a plasticized amount of the second class of gutta-percha coated thereover for introduction into a root canal.

While the foregoing discussion has focused upon methyl methacrylate as a rigidifying material, another material can be used as long as it provides the filler material with sufficient rigidity for supporting the plasticized gutta-percha positioned thereon as the gutta-percha amounts are introduced into a root canal. Accordingly, principles of the present invention may be variously applied.

As mentioned above, the second class of gutta-percha utilized herein has a plasticizing temperature which is lower than that of the aforementioned first class of gutta-percha comprising the point 50. However, the gutta-percha of this second gutta-percha material of the second class is relatively firm at room temperature, and must be heated in order to plasticize the material for application to the point 50. Although the second class of gutta-percha may be coated about the point 50 of FIG. 2 or the point 52 of FIG. 3 by any of a number of processes, the second class of gutta-percha in the depicted example is contained within an apparatus 60 illustrated in FIG. 4 within which the gutta-percha, indicated 62 in FIG. 4, may be heated to a plasticized condition and with which the gutta-percha 62 may be coated about the point 50 or 52.

The apparatus 60 resembles a syringe in structure and operation in that it includes an elongated hollow barrel 64 for containing the second class of gutta-percha 62 and a plunger 66 slidably fitted within the barrel 64. At one end of the barrel 64 is provided an opening 63 for loosely receiving the point 50 or 52 inserted end-wise therein. For a more detailed description of the structure of apparatus 60, reference may be had to U.S. Pat. No. 5,067,900, whose disclosure concerning the apparatus 60 is incorporated herein by reference.

With the gutta-percha 62 contained therein, the apparatus 60 is heated within a heating appliance 68, shown in FIG. 5, including an electrically-heated heat-conducting plate 70 having an opening 72 within which the apparatus 60 may be positioned for heating. The apparatus 60 is heated by the appliance 68 to a predetermined temperature at which the gutta-percha 62 becomes plasticized but does not exceed the plasticizing temperature of the gutta-percha of the point 50 or 52. The appliance 68 includes thermostat control knobs 74 for controlling the temperature to which the plate 70 is raised to thereby control the temperature to which the apparatus 60, and the gutta-percha contained therein, are exposed.

Upon heating the gutta-percha 62 contained within the apparatus 60 to the preselected temperature, the apparatus 60 is removed from the appliance 68 and the tip end of the point 50 or 52 is inserted by an appreciable distance into the barrel opening 63 so that a significant amount of the point 50 or 52 enters the opening 63 and engages the plasticized gutta-percha 62 contained within the barrel 64. With reference to FIG. 6, the plunger 66 is then moved with the fingers through the barrel 64 to dispense the gutta-percha 62 through the barrel opening 63 while simultaneously withdrawing the point 50 or 52 from the opening 63 in the direction of the arrow 76. Preferably, the rate at which the point 50 or 52 is withdrawn from the opening 63 is coordinated with the rate at which the plunger 66 is moved toward the opposite barrel end so that all of the gutta-percha 62 emitted from the end wall opening 63 adheres to the surface of the point 50 or 52. As mentioned earlier, the enhanced tackiness of the gutta-percha 62 when in its plasticized state is well-suited for sticking the gutta-percha 62 to the surface of the point 50 or 52. When fully withdrawn from the apparatus opening 63 as illustrated in FIG. 7, the point 50 or 52 is coated along a major portion of its length with the second class of gutta-percha 62.

Figure 8:
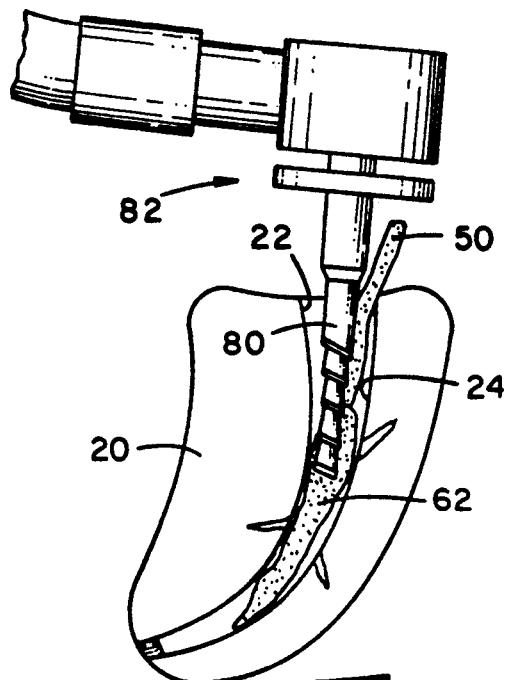

With the plasticized gutta-percha 62 coated about the point 50, the point 50 is inserted tip-end first into the extirpated space 24 of a root canal 22 (FIG. 1) for introducing both of the first and second classes of gutta-percha into the space 24. With the coated tip of the point 50 positioned within the canal, the two classes of gutta-percha are manipulated within the canal into a compacted condition by the application of pressure to the coated tip through the point 50 to displace the gutta-percha amounts within the canal. Such pressure is applied while the point 50 remains held, for example, between the jaws of an appropriate tool, such as the tool 78 of FIG. 7, and the lower portion of the point 50 is gently tapped therefore, the upper portion, as viewed in FIG. 8, of the point 50 may act as a tool for urging the lower portion of the point 50 and the amount of the second class of gutta-percha 62 coated thereabout into a mixed and spread condition within the canal. As the first and second classes of gutta-percha are worked with the shank 80, heat from the heated, second class of plasticized cooler, first class of gutta-percha is absorbed by the gutta-percha of the point 50 so that the point 50, and in particular the portions of the point 50 in direct contact with the heated, second class of plasticized gutta-percha becomes softened and bonded with the plasticized gutta-percha 62.

Figure 9:
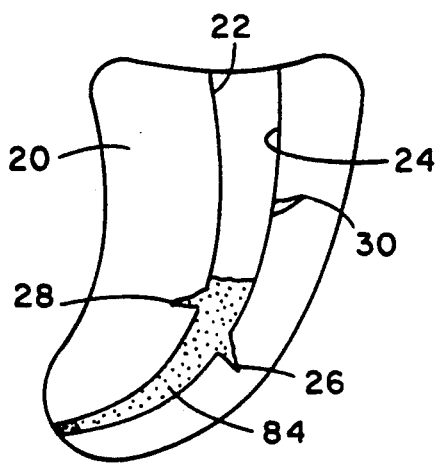

As the mixing of the material of the point 50 and plasticized material 62 continues, the instrument shank 80 is continually manipulated to work the softened material mix into a desired region of the canal space 24, and the upper portion of the point 50 is urged downwardly into the canal where it is compacted with the plasticized gutta-percha 62. If desired, the shank instrument 82 illustrated in FIG. 8, such as a compacter or spreader, may be utilized in a known manner to compact the upper portion of the point 50 with the canal. Upon completion of the compaction of the point 50 with the amount of plasticized gutta-percha 62 so that the filler material mix, indicated 84 in FIG. 9, is positioned adjacent the bottom of the canal 22, the instrument shank 80 is removed from the canal 22.

The aforementioned steps of providing a gutta-percha point 50, applying a coating of plasticized gutta-percha 62 upon the point 50, introducing and manipulating the first and second classes of gutta-percha within the canal space 24 are thereafter repeated as necessary until the root canal space 24 is completely filled with filler material. A compactor or spreading instrument may be used to ensure that filler material is urged within any remaining voids. The filled root canal may thereafter be finished by conventional techniques.

An advantage provided by the aforedescribed obturating process relates to the filling of the fissures 26, 28, 30 and similar openings defined in the wall of the extirpated root canal 22. More specifically, as the first and second classes of gutta-percha are mixed and worked against the wall of the root canal 22, the filler material of the mix flows within so as to completely fill the canal wall fissures 26, 28, 30. It is believed that such a complete filling of the fissures is effected as the plasticized gutta-percha, which is more "fluid" in its plasticized condition than is the softened material of the gutta-percha point 50, easily flows along the surface of the canal wall so as to readily conform to the shape of the canal wall and flows into the fissures 26, 28, 30 opening out of the wall. Therefore, even after mixing, the filler material mix 84 is likely to possess a perimetal layer comprised primarily of the second class of gutta-percha and a core comprised primarily of the first class of gutta-percha. When the mix 84 is subsequently cured to a solid, relatively rigid condition within the canal, the cured mix 84 is firmly held therein.

Figure 10:
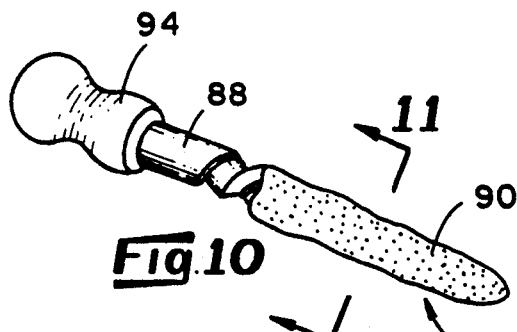
FIG. 10 is a perspective view of a carrier upon which a first class of gutta-percha material is coated.
Figure 11:
FIG. 11 is a cross-sectional view taken about along line 11—11 of FIG. 10.
Figure 12:
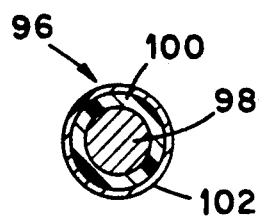
FIG. 12 is a cross-sectional view of a carrier having a gutta-percha coating like that of FIG. 10 which has been coated with a layer of methyl methacrylate.

In another aspect of the one embodiment of the method, the first class of gutta-percha is provided as a coating upon the shank of a shanked carrier. For example, there is illustrated in FIGS. 10 and 11 an assembly 92 including a shanked carrier 86 in the form, for example, of a dental file having a shank 88 which has been pre-coated with an amount of the first class of gutta-percha 90 and which has been fitted within an instrument, or handle 94. There is illustrated in FIG. 12 an alternative assembly 96 including a shank 98 which has been pre-coated with an amount of the first class of gutta-percha 100 which, in turn, has been coated with a layer 102 of a rigidifying material, such as a cured layer of methyl methacrylate. In either assembly 92 or 96, the carrier shank 88 or 98 may be constructed, for example, of steel or a hard plastic and, if the carrier is of a type which may be cut off and left within the canal, is bio-compatible.

Figure 13:
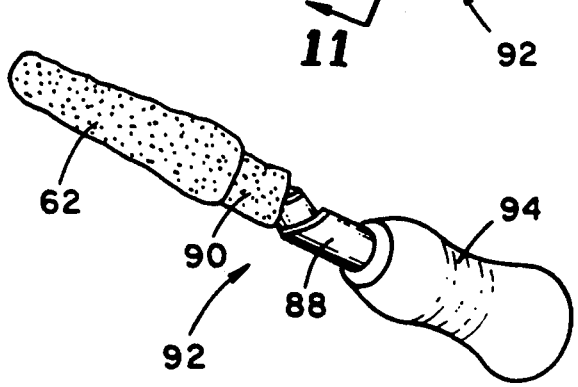
FIG. 13 is a perspective view of the carrier and gutta-percha coating of FIG. 10 upon which a second class of gutta-percha material is coated.

In accordance with this another aspect of the one embodiment of the method, the assembly 92 or 96 is coated with an amount of the second class of gutta-percha. The coating of the gutta-percha amounts 90 or 100 of the assembly 92 or 96, respectively, may be effected with the apparatus 40, as discussed above in connection with the coating of the point 50 of FIG. 2, involving the heating of the apparatus 40 containing the second class of gutta-percha 62 to its plasticizing temperature, the insertion of the assembly 92 or 96 tip-end-first into the barrel opening 63 and then moving the plunger 66 through the apparatus barrel 64 and simultaneously withdrawing the assembly 92 or 96 from the opening 63 so that the second class of gutta-percha 62 exiting the opening 63 coats the assembly 92 or 96 along a major portion of its length, as exemplified by the assembly 92 shown in FIG. 13.

The first and second amounts of gutta-percha borne by the assembly shank 88 or 98 are then introduced into a root canal by inserting the tip end of the shank of the assembly 92 or 96 into the canal. In instances in which a portion of the plasticized (i.e., second class) of gutta-percha is unintentionally wiped from the assembly shank during insertion of the shank into the canal, the underlying coating comprised of the first class of gutta-percha remains upon the shank and thereby prevents, during insertion of the assembly, the exposure of a bare, or denuded, surface of the shank to the tissue of the canal and reduces any likelihood of health risks, such as infection, which could result therefrom. Accordingly, the aforedescribed multiple coatings of gutta-percha upon the shank of the assembly is advantageous in this respect.

With the assembly 92 or 96, with the plasticized amount (i.e., second class) of gutta-percha borne thereby, is positioned within the canal, the shank of the assembly is manipulated with appropriate (e.g., rotary and reciprocating) motions to work the coatings of the first and second classes of gutta-percha downwardly and off of the end of the shank and into a compacted condition within the canal. As the shank continues to be manipulated, the first and second classes of gutta-percha are mixed so that heat from the plasticized gutta-percha is absorbed by the first class of gutta-percha to render the first class of material into a softened and more workable condition. Moreover, as the two classes of gutta-percha are mixed, the second class of gutta-percha flows along and readily conforms to the inner surface of the canal wall so as to completely fill voids and fissures which may be provided therein. Upon completion of the compaction operation involving the coating of the first class of gutta-percha of the assembly 92 or 96 and the plasticized coating of the second class of gutta-percha within the canal, the assembly shank is either removed from the canal or, if desired, cut off and left within the canal in an embedded condition within the gutta-percha mix. Thereafter, the aforementioned steps of providing an assembly 92 or 96, heating the second class of gutta-percha, coating the assembly 92 or 96 with the plasticized second class of gutta-percha, introducing the assembly 92 or 96 into the canal and manipulating the first and second classes of gutta-percha within the canal are repeated as necessary with additional assemblies like that of assembly 92 or 96 to fill the root canal with filler material.

In another embodiment of the method of the invention, there is provided an amount of the first class of gutta-percha and an amount of the second class of gutta-percha coated about the amount of the first class of gutta-percha. For example, there is illustrated in FIGS.

14 and 15 an embodiment 104 of a filler material including a core 106 comprised of the first class of gutta-percha and an outer coating 108 of the second class of gutta-percha. There is illustrated in FIG. 16 an alternative filler material embodiment 110 including a core 112 comprised of the first class of gutta-percha, an outer coating 114 comprised of the second class of gutta-percha and an intermediate layer 116 of a rigidifying material, such as a cured layer of methyl methacrylate, interposed between the core 112 and outer coating 114.

To use either of the aforementioned filler material embodiments 104 and 110 in this another embodiment of the method, the embodiment 104 or 110 is heated so that the outer coating of the second class of gutta-percha becomes plasticized but the core of the first class of gutta-percha remains unplasticized. Although the outer coating of the embodiments 104 or 110 may be heated by any of a number of processes, the outer coating of the embodiment 104 depicted in FIG. 17 is heated by means of a heating apparatus 118.

The apparatus 118 includes an electrically-heated cavity 120 having an upwardly-directed opening 122 within which the filler embodiment 104 may be inserted for heating. As the apparatus 118 is operated and the embodiment 104 is held within the cavity 120, the outer coating 108 is heated to a temperature at which the coating 108 becomes plasticized but the core 106 remains in an unplasticized condition. The apparatus 118 includes a thermostat control knob 124 for controlling the temperature to which the walls of the cavity 120 are raised to thereby control the temperature to which the outer coating 108 is exposed.

Upon heating the embodiment 104 or 110 until its outer coating 108 or 114 becomes plasticized as aforedescribed, the embodiment 104 or 110 is introduced into the space of an extirpated root canal by inserting the embodiment 104 or 110 tip-end-first within the canal. The embodiment 104 or 110 is then manipulated with appropriate motions (e.g., tapping motions) to compact its core material and its outer coating within the canal space. As was the case with the point 50 and gutta-percha amount 62 in the FIG. 8 example, the core and outer coating of the filler material embodiments 104 and 110 may be worked with the shank of an instrument into a compacted mix within the canal. The aforementioned steps of providing a filler material embodiment 104 or 110, heating its outer coating to its plasticizing temperature, introducing the embodiment 104 or 110 into a canal, and then manipulating the embodiment 104 or 110 into a compacted condition are thereafter repeated as necessary with additional embodiments like that of embodiment 104 or 110 to fill the root canal with filler material.

In another aspect of the another embodiment of the method, the first class of gutta-percha is provided as an inner coating upon the shank of a shanked carrier and the second class of gutta-percha is provided as an outer coating positioned about the inner coating. For example, there is illustrated in FIGS. 18 and 19 a filler material assembly 126 including a shanked carrier 128 in the form of a dental file having a shank 130 which may be connected to an instrument or handle, such as the handle 94 of FIG. 10, which has been pre-coated with a first coating 132 comprised of the first class of gutta-percha overlying the surface of the shank 130 and an outer coating 134 comprised of the second class of gutta-percha which has been pre-coated about the first coating 132. There is illustrated in FIG. 20 an alternative filler material assembly 136 having a shank 138 of a shanked carrier which has been pre-coated with a first coating 138 of the first class of gutta-percha positioned directly upon the surface of the shank 130, an outer coating 142 comprised of the second class of gutta-percha and an intermediate layer 144 of a rigidifying material, such as a cured layer of methyl methacrylate, interposed between the first coating 140 and outer coating 142.

To use either of the aforementioned filler material assemblies 126 or 136 in this another aspect of the another method embodiment, the assembly 126 or 136 is heated so that the outer coating of the second class of gutta-percha becomes plasticized but the first coating of the first class of gutta-percha remains unplasticized. Such a heating process may be effected, for example, with the heating apparatus 118 illustrated in FIG. 17 as the assembly 126 or 136 is supported within its heated cavity 120.

Upon heating the assembly 126 or 136 until its outer coating 134 or 142 becomes plasticized as aforedescribed, the assembly 126 or 136 is introduced into the space of an extirpated root canal by inserting the tip end of the assembly 126 or 136 into the root canal. It will be understood that the shank of the assembly 126 or 136 may be appropriately connected to a rotating instrument, such as the instrument 94 of FIGS. 10 and 13, or another suitable tool to facilitate the introduction of the assembly 126 into the root canal. With the tip end of the assembly 126 or 136 positioned within the canal, the shank 130 or 138 of the assembly is appropriately manipulated to work the first and outer coatings of the assembly 126 or 136 downwardly along and off of the shank. As the shank 130 or 138 continues to be worked against the first and outer coatings, the first and second classes of gutta-percha are mixed and compacted within the canal. When the compaction of the first and second classes of gutta-percha borne by the assembly shank 130 or 138 is completed, the shank 130 or 138 is either removed from the canal or, if desired, cut off and left within the canal. The aforementioned steps of providing an assembly 126 or 136, heating the outer coating of the assembly 126 or 136 to a plasticized condition, introducing the assembly 126 or 136 into a root canal, and manipulating the assembly shank so that its first and outer coatings become compacted within the canal are repeated as necessary to fill the root canal with filler material.

It will be understood from the foregoing that numerous modifications and substitutions may be had to the aforedescribed embodiments without departing from the spirit of the invention. Accordingly, the aforedescribed embodiments are intended for the purpose of illustration and not as limitation.

I claim:

1. A method of obturating an extirpated root canal with filler material comprising the steps of:
providing a first amount of gutta-percha which becomes plasticized at a predetermined temperature;
coating at least a portion of the first amount with a second amount of gutta-percha when the second amount is in a plasticized condition and at a preselected temperature wherein the temperature at which the second amount becomes plasticized is lower than the predetermined temperature at which the first amount becomes plasticized and the preselected temperature is less than the predetermined temperature so that the first amount remains in a relatively firm condition while the plasticized second amount remains coated thereabout; and introducing the first and second amounts together into a root canal; and manipulating the first and second amounts with rotary and reciprocating motions as necessary to feed the amounts further into the canal and thereby mix and work the amounts into a compacted condition within the canal.

2. The method as defined in claim 1 wherein the step of coating is preceded by the steps of:

providing the second amount of gutta-percha in an unplasticized condition and heating the second amount to the preselected temperature to plasticize the second amount.

3. The method as defined in claim 1 wherein the first amount is a first class of gutta-percha and the second amount is a second class of gutta-percha and the steps of coating, introducing and manipulating are repeated as necessary with additional amounts of the first and second classes of gutta-percha to fill the root canal with filler material.

4. The method as defined in claim 1 wherein the first amount is provided in the form of a point possessing sufficient rigidity following the step of coating so that during the step of introducing, the point is used to supportedly carry the plasticized second amount into the root canal.

5. The method as defined in claim 1 wherein the first amount is provided with a layer of a rigidifying material coated thereabout so that the subsequent step of coating the first amount effects a coating of the rigidifying material layer with the second amount.

6. The method as defined in claim 1 wherein the first amount is provided as a coating upon the shank of a shanked carrier so that the step of introducing includes a step of inserting the shank of the carrier, with the first and second amounts borne thereby, into the root canal.

7. The method as defined in claim 6 wherein the first amount coated about the shank of the shanked carrier is provided with a layer of a rigidifying material coated thereabout so that the subsequent step of coating the first amount effects a coating of the rigidifying material layer with the second amount.

8. The method as defined in claim 6 wherein the step of manipulating the filler material is followed by a step of removing the shank of the shanked carrier from the root canal so that the carrier is not left within the canal upon completion of an obturating process.

9. A method of obturating an extirpated root canal comprising the steps of:

providing a filler material including a first amount of gutta-percha and a second amount of gutta-percha coated about the first amount wherein the temperature at which the second amount becomes plasticized is less than the temperature at which the first amount becomes plasticized;

heating the filler material so that the second amount becomes plasticized but the first amount remains unplasticized; and introducing the filler material into a root canal and manipulating the filler material with rotary and reciprocating motions as necessary to feed the first and second amounts further into the canal and thereby mix and work the filler material into a compacted condition within the canal.

10. The method as defined in claim 9 wherein the filler material is one filler material quantity and the steps of providing, heating, introducing and manipulating are repeated as necessary with additional quantities of filler material like that of said one quantity to fill the root canal.

11. The method as defined in claim 9 wherein the filler material is provided in the form of a point having a core comprised of the first amount and possessing sufficient rigidity following the step of heating so that during the step of introducing, the point is used to supportedly carry the plasticized second amount into the root canal.

12. The method as defined in claim 9 wherein the filler material is provided as a coating positioned upon the shank of a shanked carrier so that the step of introducing includes a step of inserting the shank of the carrier, with the first and second amounts borne thereby, into the root canal.

13. A method of obturating an extirpated root canal comprising the steps of:

providing a filler material including a first amount of gutta-percha, a layer of rigidifying material coated about the first amount, and a second amount of gutta-percha coated about the layer of rigidifying material wherein the temperature at which the second amount becomes plasticized is less than the temperature at which the first amount becomes plasticized;

heating the filler material so that the second amount becomes plasticized but the first amount remains unplasticized; and introducing the filler material into a root canal and manipulating the filler material with rotary and reciprocating motions are required to feed the first and second amounts further into the canal and thereby mix and work the filler material into a compacted condition within the canal.

14. The method as defined in claim 13 wherein the filler material is one filler material quantity and the steps of providing, heating, introducing and manipulating are repeated as necessary with additional quantities of filler material like that of said one quantity to fill the root canal.

15. The method as defined in claim 13 wherein the filler material is provided in the form of a point having a core comprised of the first amount and wherein the point possesses sufficient rigidity following the step of heating so that during the step of introducing, the point is used to supportedly carry the plasticized second amount into the root canal.

16. The method as defined in claim 13 wherein the filler material is provided as a coating positioned upon the shank of a shanked carrier so that the step of introducing includes a step of inserting the shank of the carrier, with the first and second amounts borne thereby, into the root canal.

17. A filler material for obturating an extirpated root canal comprising:

a first amount of gutta-percha which becomes plasticized at a predetermined temperature; and a second amount of gutta-percha coated about the first amount wherein the second amount becomes plasticized at a temperature which is less than that of the predetermined temperature so that upon heating the filler material to a plasticized condition without plasticizing the first amount, the second amount is supported by the first amount for introduction into a root canal; and the differential between the plasticizing temperatures of the first and second amounts is within the range of about 10 to 20 Centigrade degrees.

18. The filler material as defined in claim 17 further comprising a layer of a rigidifying material interposed between the first and second amounts.

19. The filler material as defined in claim 18 wherein the rigidifying material is a cured layer of methyl methacrylate.

20. The filler material as defined in claim 17 wherein the filler material is provided in the form of a point having a core comprised of the first amount and an outer coating comprised of the second amount.

21. The filler material as defined in claim 17 wherein the filler material is provided as a coating positioned upon the shank of a shanked carrier so that the first amount is disposed between the surface of the shank and the second amount.

22. The filler material as defined in claim 21 wherein the shanked carrier is adapted to be used for introducing the filler material to an extirpated root canal but is not intended to be left within the canal upon completion of an obturating process.

23. A filler material for use when obturating an extirpated root canal, the filler material comprising:
 a first amount of gutta percha which becomes plasticized at a first predetermined temperature;
 a second amount of gutta-percha which becomes plasticized at a second predetermined temperature which is higher than the first predetermined temperature; and
 a layer of rigidifying material coated about the second amount for rigidifying the second amount so that the first amount of gutta-percha may be positioned about the second amount in a plasticized condition and at a temperature lower than the second predetermined temperature so that the coated second amount possesses sufficient rigidity for supporting the plasticized first amount of gutta-percha for introduction into a root canal, and
 the differential between the first and second predetermined temperatures is within the range of about 10 to 20 Centigrade degrees.

24. The filler material as defined in claim 23 wherein the filler material is provided in the form of a point having a core comprised of the second amount of gutta-percha and an outer coating positioned about the core comprised of the layer of the rigidifying material.

25. The filler material as defined in claim 23 wherein the filler material is provided as a coating positioned upon the shank of a shanked carrier so that the second amount of a gutta-percha is disposed between the surface of the shank and the layer of the rigidifying material.

26. The filler material is defined in claim 23 wherein the rigidifying material is a cured layer of methyl methacrylate.

* * * * *